(12) United States Patent
Mihajlova et al.

(10) Patent No.: US 10,603,255 B2
(45) Date of Patent: *Mar. 31, 2020

(54) MULTICOMPONENT MESO THREAD CONTAINING HYALURONIC ACID AND METHOD FOR PRODUCING SAME (VARIANTS)

(71) Applicant: MARTIN'EX International Research and Development Centre, Moscow (RU)

(72) Inventors: Natal'ya Pavlovna Mihajlova, Moscow (RU); Mihail Anatol'evich Selyanin, Moscow (RU); Sergej Alekseevich Uspenskij, Moscow (RU)

(73) Assignee: MARTIN'EX International Research and Development Centre, Moscow (RU)

(*) Notice: Subject to any disclaimer, the term of this patent is extended or adjusted under 35 U.S.C. 154(b) by 0 days.

This patent is subject to a terminal disclaimer.

(21) Appl. No.: 16/155,330

(22) Filed: Oct. 9, 2018

(65) Prior Publication Data

US 2019/0038518 A1 Feb. 7, 2019

Related U.S. Application Data

(63) Continuation of application No. 15/554,078, filed as application No. PCT/RU2016/000208 on Apr. 11, 2016, now Pat. No. 10,123,949.

(30) Foreign Application Priority Data

Apr. 28, 2015 (RU) .................. 2015116096

(51) Int. Cl.
| | |
|---|---|
| *A61K 8/02* | (2006.01) |
| *A61Q 19/08* | (2006.01) |
| *A61L 27/34* | (2006.01) |
| *A61L 27/36* | (2006.01) |
| *A61L 27/54* | (2006.01) |
| *A61K 8/81* | (2006.01) |
| *A61K 8/19* | (2006.01) |
| *A61L 27/20* | (2006.01) |
| *A61L 27/58* | (2006.01) |
| *A61K 8/64* | (2006.01) |
| *A61K 8/73* | (2006.01) |
| *C08L 5/08* | (2006.01) |
| *C08L 29/04* | (2006.01) |

(52) U.S. Cl.
CPC ............ *A61K 8/0233* (2013.01); *A61K 8/027* (2013.01); *A61K 8/19* (2013.01); *A61K 8/64* (2013.01); *A61K 8/735* (2013.01); *A61K 8/736* (2013.01); *A61K 8/8129* (2013.01); *A61L 27/20* (2013.01); *A61L 27/34* (2013.01); *A61L 27/3604* (2013.01); *A61L 27/54* (2013.01); *A61L 27/58* (2013.01); *A61Q 19/08* (2013.01); *C08L 5/08* (2013.01); *C08L 29/04* (2013.01); *A61L 2300/404* (2013.01); *A61L 2300/406* (2013.01)

(58) Field of Classification Search
None
See application file for complete search history.

(56) References Cited

U.S. PATENT DOCUMENTS

| | | | | |
|---|---|---|---|---|
| 5,658,915 | A * | 8/1997 | Abe ........................ | A01N 33/12 514/252.11 |
| 2005/0177103 | A1 * | 8/2005 | Hunter ................... | A61B 17/11 604/96.01 |

FOREIGN PATENT DOCUMENTS

EP 1879552 B1 * 2/2016 ............. A61K 9/204

OTHER PUBLICATIONS

Altman, Gregory H., et al. "Silk-based biomaterials." Biomaterials 24.3 (2003): 401-416. (Year: 2003).*

* cited by examiner

*Primary Examiner* — Robert J Yamasaki
(74) *Attorney, Agent, or Firm* — Nadya Reingand; Yan Hankin

(57) ABSTRACT

The group of inventions relates to the field of aesthetic, plastic and reconstructive cosmetology/medicine, and more particularly to meso threads used for remedying aesthetic and age-related changes to the skin, and to methods for producing such threads. Proposed is a multicomponent meso thread consisting of a core and a shell. The core is realized in the form of a fibroin thread, and the shell contains hyaluronic acid or a salt thereof or a polyelectrolyte complex of hyaluronic acid or a salt thereof and chitosan or a salt thereof. Also proposed are a variant of the thread having a plastifying agent in the shell, and methods for producing the proposed meso threads.

9 Claims, No Drawings

ND MESO THREAD
MULTICOMPONENT MESO THREAD CONTAINING HYALURONIC ACID AND METHOD FOR PRODUCING SAME (VARIANTS)

CROSS-REFERENCE TO RELATED APPLICATIONS

The instant application is a continuation application of U.S. Ser. No. 15/554,078 filed on Aug. 28, 2017 which is a National Phase Entry of International Patent Application No. PCT/RU2016/000208, filed on Apr. 11, 2016, and claims priority to Russian Patent Application No. 2015116096, filed on Apr. 28, 2015, the entire specifications of both of which are expressly incorporated herein by reference.

FIELD OF THE INVENTION

The group of inventions belongs to the field of aesthetic, plastic and reconstructive cosmetology/medicine, to-wit, the mesotherapeutic threads used to correct aesthetic and age-related skin changes, as well as the ways to manufacture them.

BACKGROUND OF THE INVENTION

Today, one of the directions in the industry of materials for cosmetology and plastic surgery are the development and production of mesotherapeutic threads (microthreads, 3D threads), the cosmetological threads used to perform the minimally invasive technique of threadlifting. The method consists in the subcutaneous injection of mesothreads in order to reinforce facial tissues and eliminate ptosis by means of biodegradable mesothreads that allow for modelling tissues in any areas including face and body parts that are not treatable using other technologies. A mesothread is a thread used to perform 3D modelling of face and body contours and to connect tissues to form a scar, or epithelization. Mesothreads can even out the skin relief thanks to the compressing activity of threads introduced subcutaneously. An essential condition for the bioreinforcement to have clinical effect is the creation of stringers that ensure pronounced and long-lasting lifting of the soft tissues.

Mesothreads are made using threads with a monofilament structure, high biocompatibility, optimum physical and mechanical properties (durability, stiffness, strain characteristics, thread's "memory effect") and resistance to infection. After having performed their functions and formed a normal durable scar, the mesothreads should completely degrade, their degradation products being included into the body's metabolism without negatively affecting it. In other words, the thread lifting procedure should be reversible (maintaining the effect for a period between 0.5 and 2 years) and compatible with other anti-age procedures.

At present, there are various mesothreads made from different materials. Aesthetic therapy uses skin lifting using golden threads (e.g., patent KR 1020140071885, Dec. 6, 2014). This method is efficient but still has its drawbacks. The golden threads do not biodegrade and can cause allergies because they contain metals; patients who have had their skin lifted using golden threads are not allowed to undergo most instrumental physiotherapeutic procedures and plastic surgeries anymore.

The most suitable material for making mesothreads are biodegradable polymers. One of the most widely used among them is now polydioxanone (PDO). Threads made from it have outstanding biocompatibility and degrade within 8 month, are elastic, do not produce a "saw" effect and are atraumatic.

At the technical level, the RF patent No. 2524610, published in 2014 (prototype), describing a multi-component mesothread consisting of a polydioxanone core and a coat made from polyglycolic acid, used to correct aesthetic and age-related skin changes.

Following are the drawbacks of PDO-based mesothreads: such threads fully degrade in the human organism by means of hydrolysis within 4-8 months; the intermediate hydrolysis products accumulate in the organism next to the areas where the mesothreads are injected. Since the hydrolysis products of PDO-based mesothreads have acidic nature, they cause a local decrease in the pH level of the environment and, therefore, a moderate (low to average) tissue reaction. So far, there is no way to avoid it, since PDO degrades through water hydrolysis only, where acidic environment triggers the autocatalytic effect that accelerates further degradation of PDO. Studies show that PDO suppresses the adhesion of macrophages to some extent and causes the effect of local immunosuppression in the implantation area: there is a decrease in both the levels of humoral and cell immunity, mostly NK lymphocytes. The decreased amount of NK lymphocytes results in the development of oncological diseases and aggravations in the course of viral infections.

SUMMARY OF THE INVENTION

The current invention group purports to create strong mesothreads made from natural polymers, biocompatible with body tissues and degrading within 0.5-2 years, depending on the thickness of the coating.

The technical result consists in the creation of mesothreads that are better biocompatible with human tissues and thereby ensure that there are no tissue reactions, risk of infiltration, allergies, or hematomas.

To handle this issue and ensure the technical result, a multi-component mesothread is proposed, consisting of a core and coating. The core is a thread (filaments) made from fibroin, and the coating contains hyaluronic acid (HA) or its salt, or a polyelectrolyte complex (PEC) of hyaluronic acid or its salt with chitosan or its salt.

One of the following salts of hyaluronic acid may be used: tetraalkylammonium, lithium, sodium, potassium, calcium, magnesium, barium, zinc, aluminum, copper, aurate or mixed salt, and hydrosalt of hyaluronic acid.

As chitosan, it is suggested to use chitosan with over 50% deacetylation degree. As chitosan salt, we suggest using chitosan acetate, chisotan chloride, or chitosan lactate.

The core and/or the coating may also contain plastifying agent. The plastifying agent may be, in particular, polyvinyl alcohol.

The coating may additionally contain anti-infection and/or antiseptic agent, and/or antibiotic. As the anti-infection agent, beta-(5-nitrofuril-2)-acrolein may be used. As the antiseptic, benzyldimethyl [3-(myristoylamino)propyl] ammonium chloride monohydrate is used.

The coating may additionally content a coupling (sealing) agent, being one of the following: ethyleneglycol diglycidyl ether, diethyleneglycol diglycidyl ether, triethyleneglycol diglycidyl ether, polyethyleneglycol diglycidyl ether, propyleneglycol diglycidyl ether, 1,4-butanediol diglycidyl ether, 1,6-hexandiol diglycidyl ether, genipin.

We also suggest a multi-component mesothread consisting of a core and a coating, the core being a fibroin thread and the coating containing hyaluronic acid or its salt or a polyelectrolyte complex of hyaluronic acid or its salt with chitosan or its salt, as well as polyvinyl alcohol as a plastifying agent.

We suggest a method to obtain a bicomponent mesothread consisting of a core being a fibroin thread and a coating containing hyaluronic acid or its salt. This method comprises, first, the preparation of a forming solution of hyaluronic acid or its salt, previously swollen and solved in water; after the solving, 10-40 mass % of ethyl alcohol are introduced into the solution; the ready solution is kept for 22±2 hours at the temperature of 22±2° C. up to complete readiness (until ripened) and deaeration. Then, the fibroin thread is drawn through a forming solution of hyaluronic acid or its salt and the calibrated nozzle (spinneret), and dried.

We also suggest a method to obtain a multi-component mesothread consisting of a core being a fibroin thread and a coating containing a polyelectrolyte complex of hyaluronic acid or its salt with chitosan or its salt. This method comprehends that a forming solution of hyaluronic acid or its salt is first prepared as follows: hyaluronic acid or its salt are previously swollen and solved in water; after the solving, 10-40 mass % of ethyl alcohol are introduced into the solution; the ready solution is kept for 22±2 hours at the temperature of 22±2° C. up to complete readiness and deaeration. Then, the forming solution of chitosan or its salt is prepared as follows: chitosan or its salt are previously swollen in water, then mixed gradually with an amount of concentrated acetic acid equal to the contents of chitosan; after the chitosan is solved, 10-40 mass % of ethyl alcohol are introduced. The ready solution is kept for 22±2 hours at the temperature of 22±2° C. up to complete readiness. At the first stage, the fibroin thread is drawn through a forming solution of hyaluronic acid or its salt and the calibrated nozzle, and dried. At the second stage, the thread obtained during the first one is drawn through a forming solution of chitosan or its salt or a forming solution of hyaluronic acid or its salt, in such a way that layers of hyaluronic acid or its salt went alternating with layers of chitosan or its salt. Then, the thread is drawn through a calibrated nozzle and dried. The second stage is repeated n times.

The forming solution of hyaluronic acid and/or the forming solution of chitosan is supplemented by the coupling agent (up to 10 mass % of the weight of the polymer), being one of the following: ethyleneglycol diglycidyl ether, diethyleneglycol diglycidyl ether, triethyleneglycol diglycidyl ether, polyethyleneglycol diglycidyl ether, propyleneglycol diglycidyl ether, 1,4-butanediol diglycidyl ether, 1,6-hexandiol diglycidyl ether, glutaric aldehyde, genipin.

The forming solution of hyaluronic acid or the forming solution of chitosan is supplemented by the coupling agent (polyvinyl alcohol).

DETAILED DESCRIPTION

The thread made from fibroin (preferably, silk fibroin) is highly hygroscopic and adhesive to macromolecules of both chitosan and hyaluronic acid. As the fibroin thread, the surgical silk thread can be used, containing over 99% of fibroin, without coating.

Chitosan is a linear cationic polysaccharide with high biocompatibility, as well as antibacterial, wound-healing, haemostatic and antiseptic properties. In human body, chitosan is metabolized to D-glucosamin with lysozyme. Hyaluronic acid is a linear anionic polysaccharide, one of the components of the extracellular matrix, with a high adsorbtion and water retention capacity, and a significant role in the proliferation and migration of cells.

Since polysaccharides have a very high cohesion energy level, almost all of them are non-fusible: their fusioning temperature is higher than their decomposition temperature. Polysaccharides may be processed into products, including threads, only through solutions.

A technologically simple way of obtaining threads containing HA consists in the treatment of fibrous materials with polymer (or polymer composition) solutions and subsequent evaporation of the solvent. The coating hardens through evaporation of the solvent or the dispersive medium, as well as through chemical reaction with the hardener or the precipitator. It should be noted that the technological process is determined by the requirements applying to the ready threads as to medical materials.

The presence of a chitosan macromolecule free amino group in each elementary unit (a carboxylic group for hyaluronic acid) gives them the properties of polyelectrolytes, polybases and polyacids, respectively. Therefore, when applied layer by layer, chitosan or its salt and hyaluronic acid or its salt form polyelectrolyte complexes (PECs) in the form of polyelectrolyte monolayers (PEMs). Each time a layer is applied, a small amount of polyelectrolyte is adsorbed and the superficial charge is restored. This approach is a way to form polycation-polyanion layers in the form of electrostatically sealed films, in a gradual and controlled manner. The main benefit of threads with PEC coating is that there is no need to use additional coupling agents. Polyelectrolytic complexes of hyaluronic acid with chitosan are not water-soluble, and, within a living organism, they biodegrade slower than their separate components.

The addition of polyvinyl alcohol (PVA) into the forming solution decreases its superficial tension and increases spinnability. The mesothread with PVA plastifying agent has a smoother surface, is highly elastic and a longer time of biodegradation in the organism. As plastifying agent, PVA with deacetylation degree over 99% and molecular weight of 5-100 kDa is used. The PVA aqueous solution is prepared in water bath at a temperature of 88±2° C. After the PVA is fully solved, up to 20 mass % of ethyl alcohol are introduced into the solution. The PVA is added in the form of a solution in such a way that the content of PVA constitutes 0.1-20 mass % in relation to chitosan or hyaluronic acid.

The molecular weight of the hyaluronic acid used to make the mesothread ranks between 2 and 2,000 kDa.

The molecular weight of chitosan used to make the mesothread ranks between 1 and 1,000 kDa.

In some cases, it is suggested to introduce antiseptic agents into the structure of the thread in order to give it better anti-infection properties. The antiseptic may be, e.g., myramistin (benzyldimethyl [3-(myristoylamino)propyl] ammonium chloride monohydrate), chlorhexidine, or brilliant green.

The preferable coupling agent for chitosan, hyaluronic acid and fibroin is genipin. Genipin is a chemical compound contained in gardenia fruits extract. It is an excellent coupling agent for proteins and chitosan. It has the lowest toxicity among coupling agents. Genipin gives the threads a violet color. The addition of genipin makes a thread more visible on the operation field, therefore no need to introduce dye into the thread formula. As the thread degrades, the violet disappears. Genipin has outstanding anti-inflammatory properties.

The coupling agent within the thread helps retain the water inside, making the thread more elastic and allowing it to stay within the tissues for a longer time (needed for the tissue to restore), thereby allowing to control the thread's biodegradation period.

The invention is illustrated by the following examples.

For all the solutions, the weight of the polymers was calculated based on a specific volume and concentration of the solution, considering the polymers' humidity as well.

Example 1

A silk surgical thread with a conditional number of 10/0 (true diameter 0.020-0.029 mm) is drawn through a solution of hyaluronic acid (HA concentration is 1.0 mass %, HA molecular weight is 1,000 kDa) and a calibrated nozzle with a diameter of 0.7 mm. Then, the thread passes through a thermal oven with a temperature of 100-120° C. and a 1.5 m high quench duct under 60-80° C. where it is dried. The forming speed is 3 m per minute. The resulting mesothread has a 4 mcm thick coating made of hyaluronic acid. The content of hyaluronic acid is 3%. The relative breaking strength of the thread is 15 cN/tex, breaking elongation is 18.0%, and elasticity modulus is 6 hPa. The resulting thread is a pseudomonothread that does not have capillary canals between filaments and is highly compatible with body tissues. The overall assessment of the tissue reaction is low-medium on the 15th day after the injection, and low after 4 and 6 months. The strength loss of a silk thread with coating after being introduced into the organism takes place in 2-3 months; the thread degrades completely within 4-6 months.

Example 2

A silk surgical thread with a conditional number of 8/0 (true diameter 0.040-0.049 mm) is drawn through a solution of hyaluronic acid (HA concentration is 0.5 mass %, HA molecular weight is 1,000 kDa) and a calibrated nozzle with a diameter of 0.7 mm. Then, the thread passes through a thermal oven with a temperature of 100-120° C. and a 1.5 m high quench duct under 60-80° C. where it is dried. The forming speed is 5 m per minute. The resulting thread has a 3 mcm thick coating made of hyaluronic acid. The contents of hyaluronic acid is 2%. The relative breaking strength of the thread is 20 cN/tex, breaking elongation is 18.5%, elasticity modulus is 5.8 hPa. The resulting thread is a pseudomonothread that does not have capillary canals between filaments and is highly compatible with body tissues. The overall assessment of the tissue reaction is medium on the 15th day after the injection, low-medium after 4 and 6 months, and low after 8 months. The strength loss of a silk thread with coating after being introduced into the organism takes place in 2-3 months; the thread degrades completely within 10 months.

Example 3

A silk surgical thread with a conditional number of 3/0 (true diameter 0.20-0.29 mm) is drawn through a solution of hyaluronic acid (HA concentration is 2.0 mass %, HA molecular weight is 1,000 kDa) and a calibrated nozzle with a diameter of 1.5 mm. Then, the thread passes through a thermal oven with a temperature of 110-130° C. and a 1.5 m high quench duct under 80-100° C. where it is dried. The forming speed is 2 m per minute. The resulting thread has a 15 mcm thick coating made of hyaluronic acid. The content of hyaluronic acid is 18%. The relative breaking strength of the thread is 33 cN/tex, breaking elongation is 17.0%, and elasticity modulus is 7.1 hPa. The resulting thread is a pseudomonothread that does not have capillary canals between filaments and is highly compatible with body tissues. The overall assessment of the tissue reaction is low-medium on the 15th day after the injection, low after 4 and 6 months, and low after 8 months. The strength loss of a silk thread with coating after being introduced into the organism takes place in 3-4 months; the thread degrades completely within 12 months. The thread has outstanding stress-related characteristics along with optimum tissue reaction to its presence in the organism.

Example 4

Unlike in Example 1, the thread is drawn through a solution of hyaluronic acid (HA concentration is 8.0 mass %, HA molecular weight is 30 kDa). The resulting thread has a 73 mcm thick coating made of hyaluronic acid. The contents of hyaluronic acid is 82%. The relative breaking strength of the thread is 15 cN/tex, breaking elongation is 15.1%, elasticity modulus is 8.4 hPa. The resulting thread is a pseudomonothread that does not have capillary canals between filaments and is highly compatible with body tissues. The overall assessment of the tissue reaction is low on the 15th day after the injection, and low after 4 months. The strength loss of a silk thread with coating after being introduced into the organism takes place in 1 month; the thread degrades completely within 5 months. A fibroin thread with a coating from a concentrated HA solution with low molecular weight favors the quick vascularization of reticular connective tissue under natural conditions without any traces of fibrosis, retaining the relative strength of the thread. The thread has a high elasticity modulus, thereby displaying a pronounced "memory effect". Its special feature is that its thickness is due to a polysaccharide layer of HA which actually comes into contact with the body tissues.

Example 5

Unlike in Example 4, a coupling agent is added into the forming solution of hyaluronic acid, to-wit, the 1,4-butanediol diglycidyl ether (BDDE), and myramistin as an antiseptic. The addition of BDDE makes up 1% of the weight of hyaluronic acid, the elasticity modulus is 6.4 hPa. The resulting thread has a HA-containing coating that is not water-soluble but can swell in water. The coating is 39 mcm thick. The contents of hyaluronic acid is 54%. The relative breaking strength of the thread is 19 cN/tex, breaking elongation is 25.5%. The resulting thread is a pseudomonothread that does not have capillary canals between filaments and is highly compatible with body tissues. The overall assessment of the tissue reaction is low on the 15th day after the injection, and low after 4 months. The strength loss of a silk thread with coating after being introduced into the organism takes place in 2-3 months; the thread degrades completely within 6-7 months. A fibroin thread with a HA coating where the HA is chemically sealed (not water-soluble) with low molecular weight favors the quick vascularization of reticular connective tissue under natural conditions without any traces of fibrosis, retaining the relative strength of the thread. The thread represents an optimum combination of the elasticity module and elasticity when swollen. Its capacity to retain water increases its undesirable permeability; however the presence of myramistine (antiseptic) in the formula of the thread prevents inflammations from appearing.

Example 6

A silk surgical thread with a conditional number of 11/0 (true diameter 0.010-0.19 mm) is drawn through a solution of chitosan (chitosan concentration is 1.0 mass %, 1.0 mass % for acetic acid) and a calibrated nozzle with a diameter of 1 mm. Then, the thread passes through a thermal oven with a temperature of 100-120° C. and a 1.5 m high quench duct under 60-80° C. where it is dried. The forming speed is 3 m per minute. The thread is then drawn through a solution of hyaluronic acid (HA concentration is 1.0 mass and a calibrated nozzle with a diameter of 1 mm. Then, the thread passes through a thermal oven with a temperature of 100-120° C. and a 1.0 m high quench duct under 60-80° C. where it is dried. The forming speed is 3 m per minute. In compliance with the selected conditions and application parameters (temperatures in the oven and in the quench duct, diameter of the nozzle, forming speed, concentrations of chitosan and hyaluronic acid, viscosity of the solutions), the resulting thread has a coating from a polyelectrolytic complex of hyaluronic acid and chitosan, 18 mcm thick. The contents of the PEC of hyaluronic acid and chitosan is 10%. The relative breaking strength of the thread is 16 cN/tex, breaking elongation is 16.0%, elasticity modulus is 6.8 hPa.

The resulting thread is a pseudomonothread that does not have capillary canals between filaments and is highly compatible with body tissues. The overall assessment of the tissue reaction is low on the 2nd day after the injection, low on the 15th day, and low after 3 months. The strength loss of a silk thread with coating after being introduced into the organism takes place in 2 months; the thread degrades completely within 4-5 months. A fibroin thread with coating from the PEC of hyaluronic acid and chitosan has haemostatic and antibacterial properties, favors the vascularization of the reticular connective tissue under natural conditions without forming a scar.

Example 7

Unlike in Example 6, a silk thread with a conditional number of 9/0 (true diameter 0.030-0.039 mm) is used, so the resulting thread has a coating from the polyelectrolyte complex of hyaluronic acid with chitosan, 20 mcm thick. The contents of the PEC of hyaluronic acid and chitosan is 16%. The relative breaking strength of the thread is 26 cN/tex, breaking elongation is 16.0%, elasticity modulus is 7.3 hPa. The resulting thread is a pseudomonothread that does not have capillary canals between filaments and is highly compatible with body tissues. The overall assessment of the tissue reaction is low-medium on the 2nd day after the injection, low on the 15th day, and low after 5 months. The strength loss of a silk thread with coating after being introduced into the organism takes place in 5 months; the thread degrades completely within 7-8 months. A fibroin thread with coating from the PEC of hyaluronic acid and chitosan has haemostatic and antibacterial properties, favors the vascularization of the reticular connective tissue under natural conditions without forming a scar.

Example 8

Unlike in Example 6, a silk thread with a conditional number of 4/0 (true diameter 0.15-0.19 mm) is used, so the resulting thread has a coating from the polyelectrolyte complex of hyaluronic acid with chitosan, 26 mcm thick. The overall content of PEC is 21%. The relative breaking strength of the thread is 20 cN/tex, breaking elongation is 16.5%, elasticity modulus is 7.9 hPa. The resulting thread is a pseudomonothread that does not have capillary canals between filaments and is highly compatible with body tissues. The overall assessment of the tissue reaction is low-medium on the 15th day after the injection, and low after 8 months. The strength loss of a silk thread with coating after being introduced into the organism takes place in 6 months; the thread degrades completely within 10-12 months. A fibroin thread with coating from the PEC of hyaluronic acid and chitosan has haemostatic and antibacterial properties, favors the vascularization of the reticular connective tissue under natural conditions without forming a scar. This thread stands out for its high elasticity module. After the mesothread is introduced into a subcutaneous fold, the thread tries to expand, thereby smoothing out the facial fold.

Example 9

Unlike in Example 6, the concentration of chitosan in the forming solution is 2% and the concentration of hyaluronic acid in the forming solution is 3%, so the resulting thread has a coating from the polyelectrolyte complex of hyaluronic acid with chitosan, 20 mcm thick. The overall content of PEC is 23%. The relative breaking strength of the thread is 19 cN/tex, breaking elongation is 15.5%, elasticity modulus is 9.1 hPa. The resulting thread is a pseudomonothread that does not have capillary canals between filaments and is highly compatible with body tissues. The overall assessment of the tissue reaction is low-medium on the 15th day after the injection, and low after 8 months. The strength loss of a silk thread with coating after being introduced into the organism takes place in 4 months; the thread degrades completely within 8-9 months. This thread stands out for its high elasticity module that gives the thread a "memory effect", and for its thickness, caused by many polyelectrolyte layers, getting into contact with body tissues.

Example 10

Unlike in Example 9, the forming speed is 2 m per minute and the diameter of the nozzle is 1.5 mm, so the resulting thread has a coating from the polyelectrolyte complex of hyaluronic acid with chitosan, 22 mcm thick. The overall content of PEC is 28%. The relative breaking strength of the thread is 19 cN/tex, breaking elongation is 16.0%, elasticity modulus is 10.2 hPa. The resulting thread is a pseudomonothread that does not have capillary canals between filaments and is highly compatible with body tissues. The overall assessment of the tissue reaction is low-medium on the 15th day after the injection, and low after 8 months. The strength loss of a silk thread with coating after being introduced into the organism takes place in 4 month; the thread degrades completely within 8 months. This thread stands out for its high elasticity module that gives the thread a "memory effect", and for its thickness, caused by many polyelectrolyte layers, getting into contact with body tissues.

Example 11

Unlike in Example 6, the concentration of chitosan in the forming solution is 0.5% and the concentration of hyaluronic acid in the forming solution is 3%, and the number n of the thread's passes through forming solutions of chitosan and hyaluronic acid is 3. The resulting thread has a 23 mcm thick coating made of the polyelectrolytic complex of hyaluronic acid and chitosan. The overall content of PEC is 30%. The relative breaking strength of the thread is 21 cN/tex, breaking elongation is 14.0%, and elasticity modulus is 11.4 hPa. The resulting thread is a pseudomonothread that does not have capillary canals between filaments and is highly compatible with body tissues. The overall assessment of the tissue reaction is low-medium on the 15th day after the injection, and low after 8 months. The strength loss of a silk thread with coating after being introduced into the organism takes place in 5 months; the thread degrades completely within 6-7 months. This thread stands out for its high elasticity module that gives the thread a "memory effect", and for its thickness, caused by many polyelectrolyte layers, getting into contact with body tissues.

Example 12

Unlike in Example 11, a plastifying agent is introduced into the forming solutions of chitosan and hyaluronic acid, in the form of a ready polyvinyl alcohol solution. The PVA addition makes up 20% of the mass of the forming solution, both for chitosan and for hyaluronic acid. The resulting thread has a 47 mcm thick coating made of the polyelectrolytic complex of hyaluronic acid and chitosan. The overall content of PEC is 62%. The relative breaking strength of the thread is 28 cN/tex, breaking elongation is 27.0%, elasticity modulus is 6.4 hPa. The resulting thread is a pseudomonothread that does not have capillary canals between filaments and is highly compatible with body tissues. The overall assessment of the tissue reaction is low on the 15th day after the injection, and low after 10 and 14 months. The strength loss of a silk thread with coating after being introduced into the organism takes place in 6 months; the thread degrades completely within 14-16 months. The thread stands out for its relative elasticity along with the high content of the covering polymer on the silk (fibroin) thread, and the smoothness of the thread's surface means it is atraumatic.

Example 13

Unlike in Example 11, a forming solution of hyaluronic acid with PVA is prepared separately. The concentration of hyaluronic acid is 8% and the concentration of PVA is 0.3%. To make the HA solution, it is proposed to use HA with a molecular weight of 30 kDa and PVA with a molecular weight of 2 kDa. After 3 passages of the thread through forming solutions and the drying area, a nozzle with a diameter of 2 mm is installed. During the 4th passage, the ready thread with chitosan-hyaluronic coating is drawn through the HA-PVA solution. The resulting thread has a 96 mcm thick coating made of the polyelectrolytic complex of hyaluronic acid and chitosan. The polymer content is 115%. The relative breaking strength of the thread is 14 cN/tex, breaking elongation is 10.0%, elasticity modulus is 15.6 hPa. The resulting thread is a pseudomonothread that does not have capillary canals between filaments and is highly compatible with body tissues. The overall assessment of the tissue reaction is low-medium on the 15th day after the injection, and low after 8 months. The strength loss of a silk thread with coating after being introduced into the organism takes place in 8 months; the thread degrades completely within 14-15 months. This thread stands out for its high elasticity module that gives the thread a "memory effect", no rough surface of the thread, and for its thickness, caused by multiple polyelectrolyte layers, getting into contact with body tissues.

Example 14

Unlike in Example 13, a solution of chitosan lactate is made (concentration for chitosan 1.0 mass %, 2.0 mass % for lactate), and a coupling agent genipin is introduced into the forming solution of hyaluronic acid, in the amount of 0.01% of the mass of polymer chitosan. The resulting thread has a 105 mcm thick coating made of the polyelectrolytic complex of hyaluronic acid and chitosan lactate. The polymer content is 130%. The relative breaking strength of the thread is 18 cN/tex, breaking elongation is 16.0%, elasticity modulus is 12.1 hPa. The resulting thread is a pseudomonothread that does not have capillary canals between filaments and is highly compatible with body tissues. The overall assessment of the tissue reaction is low-medium on the 15th day after the injection, low-medium after 8, and low after 12 months. The strength loss of a silk thread with coating after being introduced into the organism takes place in 6 months; the thread degrades completely within 10-12 months. This thread stands out for its moderate elasticity module that gives the thread a "memory effect", no rough surface of the thread, and for its thickness, caused by multiple polyelectrolyte layers, getting into contact with body tissues, and, finally, its increased water retaining capacity. A therapeutic amount of lactic acid (lactate) in the formula of the thread improves blood circulation and, therefore, formation of new tissue. The addition of genipin makes a thread more visible on the operation field, therefore no need to introduce dye into the thread formula. As the thread degrades, the violet disappears. Genipin has outstanding anti-inflammatory properties.

The maximum amount of the coating in the form of hyaluronic acid or its salt or the polyelectrolytic complex of hyaluronic acid with chitosan or its salt may result in a weight increase of 100-130%. In this way, a mesothread is obtained that is a multi-component thread with a core-coating structure.

As seen from the examples, the proposed mesothreads have the following characteristics:
i. have a smooth and even surface and are therefore atraumatic;
ii. do not absorb the punch channel and do not stick to its walls;
iii. are highly biocompatible with human body tissues;
iv. eliminate the risk of infiltration, allergies or haematomae;
v. the hydrolysis products of such threads do not accumulate in the body, do not cause any tissue reactions and participate in the restoration of cells and tissues.

The threads are monofilament, are not water-soluble and have a "memory effect", tending to keep the initial shape of the thread. A thread always tries to straighten. The "thread memory" effect is one of the main features of mesothreads. After the mesothread is introduced into a subcutaneous fold, the thread tries to expand, thereby smoothing out the facial fold.

What is claimed is:

1. A multicomponent mesothread, comprising:
a core and a coating,
wherein the core is a fibroin thread,
wherein the coating comprises a polyelectrolyte complex of hyaluronic acid or its salt with chitosan or its salt, and
wherein the coating has a thickness of 18-105 micrometers.

2. The multicomponent mesothread according to claim 1, wherein the hyaluronic acid salt comprises at least one of tetraalkylammonium, lithium, sodium, potassium, calcium, magnesium, barium, zinc, aluminum, copper, aurate, and hyaluronic acid hydrosalt.

3. The multicomponent mesothread according to claim 1, wherein the chitosan comprises a chitosan with a deacetylation degree over 50%, and the chitosan salt comprises chitosan acetate, chitosan chloride, or chitosan lactate.

4. The multicomponent mesothread according to claim 1, wherein the core and/or coating additionally contains a plastifying agent.

5. The multicomponent mesothread according to claim 4, wherein the plastifying agent comprises polyvinyl alcohol.

6. The multicomponent mesothread according to claim 1, wherein the coating additionally contains an antiinfection agent and/or an antiseptic and/or an antibiotic.

7. The multicomponent mesothread according to claim 1, wherein the coating additionally contains an antiinfection agent, wherein the antiinfection agent comprises beta-(5-nitrofuryl-2)-acrolein.

8. The multicomponent mesothread according to claim 1, wherein the coating additionally comprises an antiseptic agent, wherein the antiseptic agent comprises benzyldimethyl [3-(myristoylamino)propyl] ammonium chloride monohydrate.

9. The multicomponent mesothread of claim 1, wherein the polyelectrolyte complex comprises polycation-polyanion layers, each one of said layers being an electrostatically sealed film.

* * * * *